United States Patent [19]

Hackler et al.

[11] 4,304,756
[45] Dec. 8, 1981

[54] APPARATUS FOR THE CATALYTIC REACTION OF $H_2$-CONTAINING FEED GAS

[75] Inventors: Erich Hackler, Essen-Kettwig; Wolfgang Schmidt, Essen, both of Fed. Rep. of Germany

[73] Assignee: Didier Engineering GmbH, Essen, Fed. Rep. of Germany

[21] Appl. No.: 142,614

[22] Filed: Apr. 21, 1980

Related U.S. Application Data

[62] Division of Ser. No. 966,751, Dec. 5, 1978, abandoned.

[30] Foreign Application Priority Data

Dec. 10, 1977 [DE] Fed. Rep. of Germany ....... 2755173

[51] Int. Cl.³ .......................... F28D 7/00; B01J 19/24
[52] U.S. Cl. ..................................... 422/200; 422/235
[58] Field of Search ............... 422/189, 190, 193, 198, 422/200, 212, 235

[56] References Cited

U.S. PATENT DOCUMENTS

| | | | |
|---|---|---|---|
| 2,159,077 | 5/1939 | Duftschmid et al. | 260/449 L |
| 2,207,581 | 7/1940 | Duftschmid et al. | 260/449.6 |
| 2,373,501 | 4/1945 | Peterson | 260/667 |
| 2,474,583 | 6/1949 | Lewis, Jr. | 260/449.6 |
| 3,989,734 | 11/1976 | Alpert et al. | 260/449.6 |

*Primary Examiner*—William A. Cuchlisksi, Jr.
*Attorney, Agent, or Firm*—Wenderoth, Lind & Ponack

[57] ABSTRACT

A $H_2$-containing feed gas is introduced into a reaction area including a liquid medium containing a catalyst, to thereby preform a catalytic reaction to produce a gaseous reaction product and to generate heat of reaction which is transferred to the liquid medium, such that the catalytic reaction occurs at an operational temperature and at an operational pressure. The liquid medium is a reactor liquid which is stable during the catalytic reaction and which boils at the operational temperature and operational pressure. The boiling reactor liquid thereby maintains the catalyst at a constant temperature. Boiling of the reactor liquid produces an evaporation of the reactor liquid, and the resultant vapor is condensed in a condensation area located above the reaction area. The thus formed condensate is retuthe catalyst at a constant temperature. Boiling of the reactor liquid produces an evaporation of the reactor liquid, and the resultant vapor is condensed in a condensation area located above the reaction area. The thus formed condensate is returned to the reaction area.

6 Claims, 1 Drawing Figure

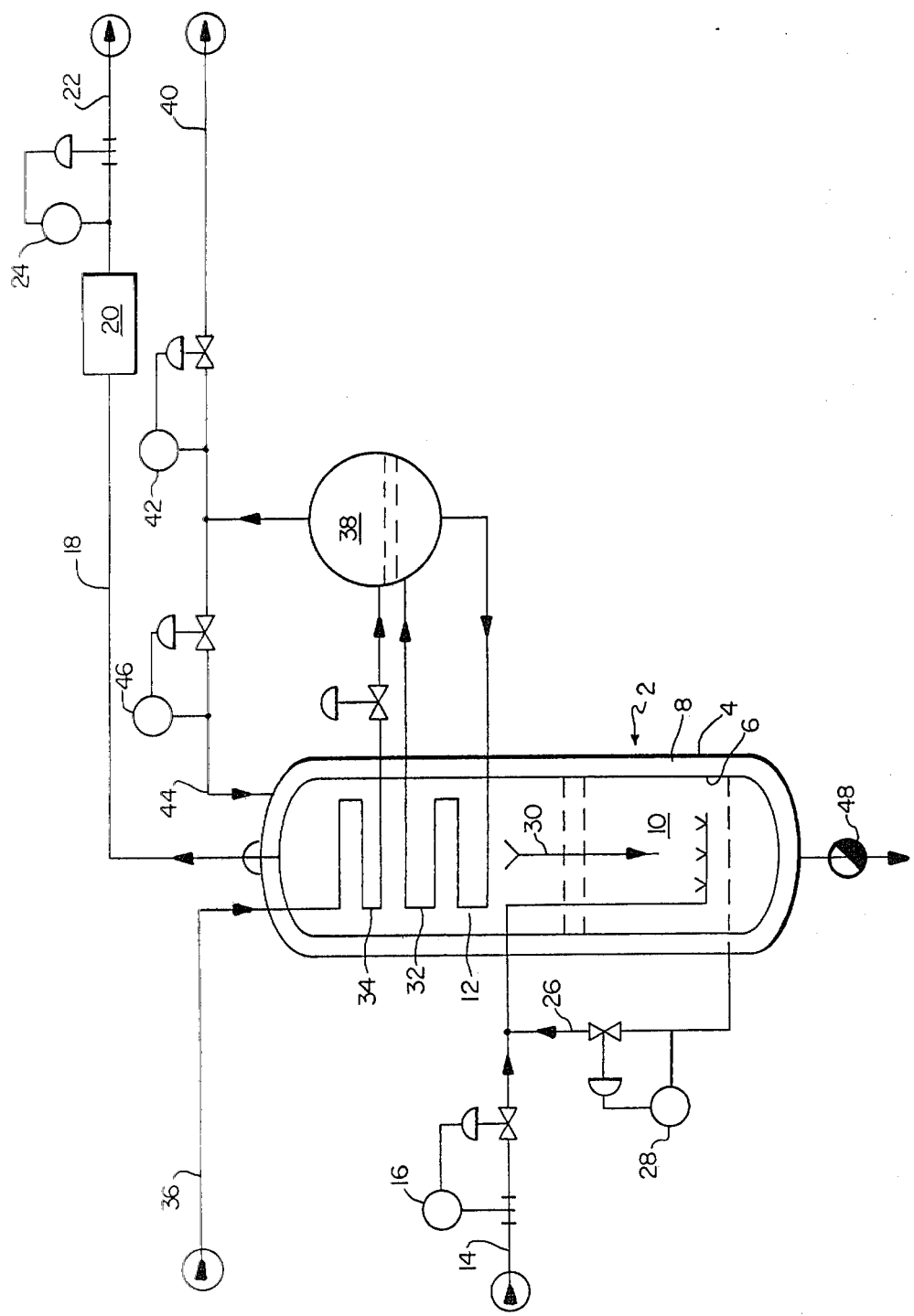

APPARATUS FOR THE CATALYTIC REACTION OF H₂-CONTAINING FEED GAS

This is a division of application Ser. No. 966,751, filed Dec. 5, 1978, now abandoned.

BACKGROUND OF THE INVENTION

The present invention relates to an apparatus for the catalytic reaction and transformation of a $H_2$-containing feed gas, wherein a catalyst is contained in a liquid medium within a reaction area, and wherein the feed gas is introduced into the liquid medium and the catalyst, to thereby perform a catalytic reaction to produce a gaseous reaction product and to generate heat of reaction.

Systems of this general type are known. For example, the article of Kölbel and Ackermann, "Large Scale Industrial Experiments Relating to Fischer-Tropsch Synthesis in a Liquid Medium", Chemie-Ingenieur-Technik, 1956 (6), page 381 and following pages, particularly page 383, left column, suggests a liquid phase synthesis by means of a suspended iron catalyst for the Fischer-Tropsch method of synthesis by means of a displaced catalyst which is suspended in the upward flow of a liquid medium. The liquid medium employed in this known process is an oil which absorbs the heat of reaction in the reaction area and is then cooled by being pumped out of the reactor through a recycling system. According to this article, difficulties result due to abrasion or decomposition of the grains of the catalyst and due to depositing of the catalyst in the recycling system.

Such disadvantages should be eliminated with the known bubble column, wherein a stationary liquid column is employed in the reaction area. However, the use of a bubble column has the disadvantage of difficulty in achieving removal of heat, similar to known gas-solid systems. Such disadvantage may readily lead to an overheating of the reaction area and to destruction of the catalyst. In the case of fluidized bed arrangements, the further disadvantages of catalyst abrasion and dust occur.

From the article of Langensiepen and Hammer, "Concerning the Dynamic Properties of a Bubble Column Reactor Comprising a Suspended Catalyst for the Methanation of Carbon Monoxide", Chemie-Ingenieur-Technik, 1974 (24), page 1051, it is known to use a bubble column reactor for the methanation of carbon monoxide. However, in a manner similar to that of Fischer-Tropsche synthesis, difficulties occur in obtaining good heat transfer. That is, heat transfer is very low in the fluidized or fluid bed, and thus extraordinarily large heat exchange surfaces are required for sufficient cooling.

Consequently, all known prior art systems are inherently limited with regard to production capacity, either due to an inherent limitation in the maximum amount of heat which can be removed, or due to abrasion of the catalyst and its removal. Prior art systems which attempt to accommodate for these disadvantages inherently increase the cost of production.

SUMMARY OF THE INVENTION

With the above discussion in mind, it is the primary object of the present invention to provide an apparatus which overcome the disadvantages of prior art systems.

It is a more specific object of the present invention to provide an apparatus for the catalytic reaction of a $H_2$-containing feed gas, wherein the feed gas is introduced into a catalyst contained within a reactor liquid which is stable during the catalytic reaction and which boils at the operational temperature and operational pressure of the catalytic reaction.

It is a further object of the present invention to provide such an apparatus whereby the boiling reactor liquid maintains the catalyst at a constant temperature, thereby avoiding overheating of the catalyst.

Thus, in accordance with the present invention, the $H_2$-containing feed gas is introduced into the reactor liquid and the catalyst, to thereby perform a catalytic reaction to produce a gaseous reaction product and to generate heat of reaction which is transferred to the reactor liquid which thus boils. Boiling of the reactor liquid produces a reactor liquid vapor which is then condensed to form condensed reactor liquid which is returned to the reactor liquid in the reaction area. This avoids both a loss of the reactor liquid and also a loss of the catalyst.

The reactor liquid vapor is condensed in a condensation area positioned above the reaction area, thereby eliminating the necessity of a special piping system to return the condensate to the reaction area. In accordance with the present invention the condensate is automatically returned to the reaction area, basically by gravity.

In accordance with a specific feature of the present invention, the condensed reactor liquid may be collected and returned to the reaction area by a collection device arranged below the condensation area.

In accordance with a further specific feature of the present invention, the reactor liquid vapor is condensed by passing a cooling agent through the condensation area in indirect heat exchange relation with the reactor liquid vapor, whereby the cooling agent absorbs the heat of reaction from the reactor liquid vapor.

The thus absorbed heat of reaction may be employed for generating steam.

The cooling agent may include water which is transformed into steam by absorbing the heat of reaction, and the water may include a lower portion of boiling water and an upper portion of relatively cooler water. By this arrangement, the reactor liquid vapor is cooled by stages, thereby avoiding overheating of the heat exchanger containing the water.

In accordance with a further specific feature of the present invention, the reaction area and condensation area are within a double-wall reactor vessel which has a space between its walls. At least a portion of the steam produced during the condensation operation is introduced into the space between the walls of the vessel. This avoids any detrimental effect exerted by carbon monoxide and/or hydrogen on the outer wall of the vessel.

The reactor liquid is a liquid which is stable with respect to the catalytic reaction. As employed herein the term "stable" is intended to mean that the reactor liquid will not undergo a change in its chemical composition during the catalytic reaction. For example, the reactor liquid should be thermally stable during the particular catalytic reaction involved, and the reactor liquid should be fully hydrogenated.

The reactor liquid may include at least one member selected from the group consisting of branched acyclic aliphatic hydrocarbons, straight chain aliphatic hydrocarbons, cycloaliphatic hydrocarbons, and aromatic hydrocarbons. It is specifically intended to be within the scope of the present invention that the reactor liquid may include a mixture of liquids, which is stable during the catalytic reaction and which boils at the operational temperature and operational pressure of the catalytic reaction. Thus, it is possible to select and predetermine the specific boiling temperature of the reactor liquid employed in a given system.

The feed gas may be serially passed through plural reaction areas, with each reaction area including a separate reactor liquid containing a catalyst. The different reactor liquids may have different boiling temperatures. This makes it possible to design an overall installation which may be infinitely variable as required by the desired catalytic reactions, the particular composition of the feed gases employed, the particular compositions of the gaseous reaction products resulting from the catalytic reactions, and the particular operational temperatures and pressures employed in a given process.

The catalyst may be suspended in the reactor liquid, or the catalyst may be contained as a fixed bed in the reactor liquid. In both cases, the catalyst will inherently be prevented from in any way being removed from the reactor liquid. Specifically, the catalyst will not be carried from the reactor liquid with the reactor liquid vapor.

BRIEF DESCRIPTION OF THE DRAWING

Other objects, features, advantages and possibilities of utilization of the present invention will be apparent from the following detailed description, taken with the accompanying drawing, wherein:

The single FIGURE is a schematic flow diagram of an installation in accordance with the present invention.

DETAILED DESCRIPTION OF THE INVENTION

The following description will specifically be made with reference to a methanation catalytic reaction. However, it is specifically to be understood that the apparatus of the present invention is by no means limited to this specific type of reaction. Rather, the apparatus of the present invention is employable in any known process and apparatus for the catalytic reaction and transformation of a $H_2$-containing feed gas.

It is specifically to be understood that the particular composition of the feed gas, the particular composition of the catalyst, the particular composition of the reactor liquid, and the particular composition of the gaseous reaction product do not in and of themselves constitute the present invention. Rather, the present invention is intended to be applicable to the use of known catalysts for the catalytic reaction of known $H_2$-containing feed gases to form by known reactions known gaseous reaction products. Furthermore, the present invention is intended to encompass the use of any reactor liquid which is stable during the catalytic reaction and which boils at the operational temperature and the operational pressure at which the catalytic reaction occurs. It is believed that those of ordinary skill in the art, upon studying the present disclosure, will readily be able to determine what reactor liquids may be employed in conjunction with particular catalysts to achieve the catalytic reaction of particular $H_2$-containing feed gases to form desired gaseous reaction products.

Returning now to the drawing, a double-wall reactor vessel 2 includes an outer wall 4 and an inner wall 6 with a space 8 therebetween. Within the vessel 2 are provided a lower reaction area 10 and an upper condensation area 12. Within reaction area 10 there is arranged a liquid medium in the form of a reactor liquid which contains a catalyst. A particular $H_2$-containing feed gas is introduced into the reactor liquid and catalyst within reaction area 10 by means of a feed pipe 14 which may be provided with a pressure regulating device 16.

There thereby occurs a catalytic reaction which produces a gaseous reaction product which rises above reaction area 10 and passes through condensation area 12 and is withdrawn through pipe 18 to a consuming network or position of utilization. The gaseous reaction product may be treated for example by being subjected to a cooling operation or a $CO_2$-washing operation as at 20 and is then discharged through a pipe 22, which also may be equipped with a pressure regulating device 24, thereby maintaining the pressure within the entire system at a desired pressure level.

In the contemplated methanation catalytic reaction, the feed gas will primarily include hydrogen and up to approximately 50% by volume of CO, $CO_2$ and $CH_4$. Again however, it is to be understood that it is not intended that the present invention be limited to a specific feed gas composition, and that other compositions may be employed in the present invention as will be understood by those skilled in the art.

Further in accordance with the specific methanation operation, the reactor liquid within reaction area 10 may be petroleum fraction between n-decane and $C_{12}H_{26}$. The operational temperature will be approximately 625° K., and the operational pressure will be approximately 50 bar. However, it is again to be understood that the present invention is not limited to such specific temperature and pressure, and that other temperatures and pressures as will be understood by those skilled in the art may be employed. For example, the temperature may be between approximately 500° K. and 750° K. and the pressure may be from approximately 5 to 200 bar. Under these conditions, the introduction of the feed gas into the catalyst will thereby result in a catalytic reaction, and the heat of reaction of such catalytic reaction will be transferred to the reactor liquid, whereby the reactor liquid will boil. This boiling of the reactor liquid will maintain the catalyst contained within the reactor liquid at a constant temperature, thereby avoiding overheating of the catalyst.

In the event that the feed gas contains a higher proportion of CO than corresponding to the stoichiometric ratio, then steam may be added via pipe 26 to the feed gas within pipe 14. Pipe 26 may be provided with a pressure regulating device 28. The thus introduced steam converts the excess CO into $H_2$ and $CO_2$.

As will be understood by those skilled in the art, the specifically discussed methanation catalytic reaction will result in a gaseous reaction product exiting through a pipe 18 having a composition of primarily $CH_4$, $CO_2$, $H_2O$ and traces of $H_2$ and CO. Again however, the present invention is not intended to be limited to a specific composition of the gaseous reaction product, and other gaseous reaction products as will be understood by those skilled in the art may result.

The boiling of the reactor liquid will produce a reactor liquid vapor which rises above reaction area 10 into condensation area 12. This vapor is condensed within condensation area 12 and thus drops substantially by gravity and is returned to the reactor liquid within reaction area 10. Thus, the loss of the reactor liquid is avoided, and also there is no need for employing complicated piping systems for returning the condensed reactor liquid to the reaction area.

In accordance with a specific feature of the present invention, the condensed reactor liquid may be collected and returned to the reaction area 10 by a collection device, schematically illustrated at 30, and equipped with a trapping funnel.

In accordance with a specific feature of the present invention, the reactor liquid vapor within condensation area 12 is condensed by means of heat exchangers 32 and 34, which are employed for the generation of high pressure steam. Specifically, upper heat exchanger 34 is supplied with relatively cool water via pipe 36, and this relatively cooler water is heated by absorbing the heat of reaction from the vapor within condensation area 12. The thus heated water is supplied in a controllable manner to steam boiler 38. Lower heat exchanger 32 is traversed by relatively hot water through a pipe system connected to the steam boiler 38. By this arrangement, the reactor liquid vapor is condensed in stages. That is, the vapor first passes in heat exchange relationship with the relatively hotter or boiling water passing through heat exchanger 32, and the vapor is thereafter further cooled by passing in heat exchange relationship with the relatively cool water passing through heat exchanger 34. The resultant condensate is returned to reaction area 10 in the manner discussed above. This condensation by stages also prevents overheating of the heat exchangers and the feed and discharge systems associated therewith.

The high pressure steam formed in steam boiler 38 can then be led to a consumer location or position of utilization through pipe 40 which may be equipped with a pressure regulating device 42. Alternatively, or in addition, at least a portion of the high pressure steam from steam boiler 38 may be supplied via pipe 44 equipped with a pressure regulating device 46 to space 8 between walls 4 and 6 of vessel 2. The pipe 26, discussed above, may open into space 8 and withdraw steam therefrom. Any condensate formed within space 8 may be withdrawn through drain 48.

Accordingly, in accordance with the present invention, the heat of reaction occurring during the catalytic reaction and transformation of the $H_2$-containing charge or feed gas is absorbed directly in situ by the boiling of the reactor liquid and is removed in the form of reactor liquid vapor. Due to the reactor liquid boiling during the catalytic reaction, the entire volume of the reaction area 10 is maintained at a desired constant temperature. The heat of reaction removed with the reactor liquid vapor is employed for the production of high pressure steam. The reactor liquid vapor is not lost, but rather is condensed and returned again to the reaction area.

The installation described above and illustrated in the drawing may readily be employed for a serial installation including plural serially connected reaction areas, each separated by a condensation area, with the feed gas sequentially being supplied through the serially connected reaction areas and condensation areas. In such an arrangement, different reactor liquids having different boiling temperatures may be employed. This specifically may be achieved by forming each reactor liquid of a mixture of different proportions of various liquids. It is thereby possible to precisely predetermine the particular equilibrium temperature required for the preparation of a particular desired gaseous reaction product. It is believed that one of ordinary skill in the art would readily understand the particular chemical reactions and necessary proportioning calculations necessary to design such an installation.

By the apparatus of the present invention, very good heat transfer is obtained by the direct transformation of the heat of reaction to heat of evaporation. The possibility of overheating of the catalyst is avoided. No catalyst will pass out of the boiling reactor liquid.

Accordingly, it is possible to avoid the disadvantages of prior art systems, even though in accordance with the present invention it is possible to employ either fine grained or coarse grained catalysts in the reactor liquid.

Further in accordance with the present invention, the cooling and condensation of the reactor liquid vapor is highly efficient.

The apparatus of the present invention may be readily adapted to particular catalytic reactions involving particular known catalysts and particular known $H_2$-containing feed gases to result in the catalytic production of particular gaseous reaction products.

The particular catalysts employed, as indicated above, do not form a portion of the present invention, but catalysts which are usable may be a wide range of nickel catalysts from raney-nickel to nickel-carrier catalysts. Again however, it is to be understood that those of ordinary skill in the art will readily understand other different catalysts which may be employed in the apparatus of the present invention.

Due to the arrangement of the present invention the heat exchange surfaces for cooling are greatly reduced as compared with known systems. This advantage, in addition to the increased production possible with the system of the present invention, substantially lowers the costs both of investment and of operation.

Although the present invention has been described and illustrated with respect to a preferred apparatus, it is to be understood that various modifications may be made to such specifically described and illustrated apparatus features, without departing from the scope of the present invention.

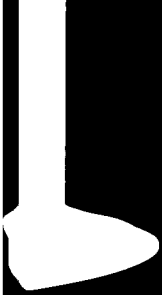

What we claim is:

1. In an apparatus for the catalytic methanation of a feed gas containing $H_2$ and CO, said apparatus being of the type including at least one reaction area including a liquid medium containing a catalyst, and means for introducing a feed gas into said liquid medium and said catalyst, to thereby perform a catalytic reaction to produce a gaseous reaction product and to generate heat of reaction which is transferred to said liquid medium, whereby said catalytic reaction occurs at an operational temperature and an operational pressure, the improvement wherein:

said liquid medium is an extraneous liquid medium comprising a reactor liquid which is stable during said catalytic reaction and which boils at said operational temperature and said operational pressure, producing a reactor liquid vapor, whereby the thus boiling reactor liquid comprises means for maintaining said catalyst at a constant temperature, and said apparatus further comprises a condensation area positioned above said reaction area in which said reactor liquid vapor is condensed to form condensed reactor liquid, means for passing a cooling agent comprising water through said condensation area in indirect heat exchange relation with said reactor liquid vapor, whereby said cooling agent absorbs the heat of reaction from said reactor liquid vapor, means for returning said condensed reactor